United States Patent
You

(10) Patent No.: US 10,115,908 B2
(45) Date of Patent: Oct. 30, 2018

(54) IMIDAZOLE[4,5-F][1,10]PHENANTHROLINE DERIVATIVES, METHOD OF PREPARING THE SAME, AND USE THEREOF

(71) Applicant: BOE Technology Group Co., Ltd., Beijing (CN)

(72) Inventor: Juanjuan You, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 743 days.

(21) Appl. No.: 14/422,901

(22) PCT Filed: Aug. 22, 2014

(86) PCT No.: PCT/CN2014/085041
§ 371 (c)(1),
(2) Date: Feb. 20, 2015

(87) PCT Pub. No.: WO2015/043346
PCT Pub. Date: Apr. 2, 2015

(65) Prior Publication Data
US 2015/0263295 A1    Sep. 17, 2015

(30) Foreign Application Priority Data
Sep. 30, 2013   (CN) .......................... 2013 1 0460740

(51) Int. Cl.
*H01L 51/54*     (2006.01)
*C07D 471/14*    (2006.01)
*H01L 51/00*     (2006.01)
*H01L 51/50*     (2006.01)

(52) U.S. Cl.
CPC ........ *H01L 51/0072* (2013.01); *C07D 471/14* (2013.01); *H01L 51/0054* (2013.01); *H01L 51/0067* (2013.01); *H01L 51/0068* (2013.01); *H01L 51/0058* (2013.01); *H01L 51/5016* (2013.01); *H01L 51/5024* (2013.01)

(58) Field of Classification Search
CPC .. C07D 471/14; C07D 209/56; C07D 403/04; C07D 471/16; H01L 51/006; H01L 51/0067; H01L 51/0072; H01L 51/5048
USPC ....... 546/64; 428/336, 411.4, 690, 691, 917; 313/500–512; 257/40, 88–104; 257/E51.001–E51.052; 252/301.16–301.35; 427/58, 66
See application file for complete search history.

(56) References Cited

U.S. PATENT DOCUMENTS

2004/0209117 A1   10/2004   Aziz et al.

FOREIGN PATENT DOCUMENTS

| CA | 2425819 A1 | 10/2004 |
|----|------------|---------|
| CN | 1753967 A | 3/2006 |
| CN | 102276607 A | 12/2011 |
| CN | 102617617 A | 8/2012 |
| CN | 103497190 A | 1/2014 |
| KR | 20140008024 A * | 1/2014 |

OTHER PUBLICATIONS machine translation of KR 20140008024 A.*
machine translation of KR 20140008024 A, Jan. 2014 (Year: 2014).*
Apr. 18, 2017—(EP) Extended European Search Report Appn No. 14850030.9.
Zhi Qiang Gao, et al, "New Host Containing Bipolar Carrier Transport Moiety for High-Efficiency Electrophosphorescence at Low Voltages", Advanced Materials, vol. 21, No. 6, (Feb. 9, 2009), pp. 688-692.
Apr. 5, 2016—International Preliminary Report on Patentability Appn PCT/CN2014/085041.
Nov. 2, 2014—(CN)—First Office Action for Appn 201310460740.9 with Eng Tran.
Apr. 20, 2015—(CN) Second Office Action for 201310460740.9 with Eng Tran -.
Shanji, "Synthesis and Properties of a Luminescent Europium Complex Containing a New Second Ligand" ACTA Scientiarum Naturalium Universitatis Sunyatseni, vol. 48, No. 2, Mar. 2009.
International Search Report and Written Opinion dated Nov. 19, 2014 (PCT/CN2014/085041); ISA/CN.

* cited by examiner

*Primary Examiner* — Jennifer A Chriss
*Assistant Examiner* — Elizabeth M. Dahlburg
(74) *Attorney, Agent, or Firm* — Banner & Witcoff, Ltd.

(57) ABSTRACT

Disclosed is an imidazole[4,5-f][1,10]phenanthroline derivative conforming to the chemical structural formula of:

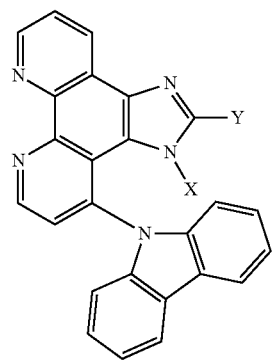

Wherein X and Y are independently selected from the group consisting of Z-substituted aryl ring, Z-substituted heteroaryl ring, unsubstituted aryl ring, or unsubstituted heteroaryl ring, and wherein Z is independently selected from the group consisting of aryl, $C_{1-4}$ alkoxy, amino, nitro, trifluoromethyl, cyano, halo atom, or $C_{1-24}$ aliphatic hydrocarbyl. The present invention further discloses a method of preparing the imidazole[4,5-f][1,10]phenanthroline derivative and the use thereof.

16 Claims, No Drawings

IMIDAZOLE[4,5-F][1,10]PHENANTHROLINE DERIVATIVES, METHOD OF PREPARING THE SAME, AND USE THEREOF

The application is a U.S. National Phase Entry of International Application No. PCT/CN2014/085041 filed on Aug. 22, 2014, designating the United States of America and claiming priority to Chinese Patent Application No. 201310460740.9 filed on Sep. 30, 2013. The present application claims priority to and the benefit of the above-identified applications and the above-identified applications are incorporated by reference herein in their entirety.

INVENTION FIELD

Embodiments of the present invention relate to imidazole [4,5-f][1,10]phenanthroline derivatives, methods of preparing the same, and use thereof.

BACKGROUND

Until now, displays used in the practical applications comprise primarily Cathode Ray Tube Display (CRT), Liquid Crystal (LCD), Vacuum Fluorescent Display (VFD), Plasma Display Panel (PDP), Organic Light Emitting Display (OLED), Field emission display (FED), Electroluminescent Display (ELD), and so on. OLED is a novel flat display, and has advantages including thinness, light weight, wide viewing angle, active light emitting, continuously adjustable emitting colors, low cost, fast response time, low energy consumption, low driving voltage, wide window of operating temperature, simple production process, high luminous efficiency, flexible display, etc., as compared to LCD. Because of unique advantages over other displayers and good application prospect of OLED, it gets substantial attention of industrial and scientific communities.

The current OLED devices comprise sequentially arranged cathode, electron transfer layer, light emitting layer, hole transport layer, anode, and substrate. Of those, the materials of light emitting layer are preferably host-guest doped emitters comprising host light-emitting materials (host materials) and doping light-emitting materials (dopants). Such host-guest doped emitters separate the transport function of carriers from the light-emitting mechanism, and utilize reasonable collocation of energy levels and interfaces between the host and the guest to optimize the properties thereof, thereby optimizing the performances of the devices. Currently, such doped systems have extended from fluorescent systems to phosphorescent systems, and achieve nearly 100% inner quantum efficiency, so as to make the industrialization of OLED possible.

From the viewpoint of energy level requirement, the energy gap of the host materials should be higher than the dopants, namely, the energy is transferred from the host materials to the dopants so that the dopants are excited for luminescence. Moreover, the phosphorescence doped systems further require that the host materials have higher triplet energy level ($E_T$) than the dopants, and otherwise the energy of the phosphorescence will be reversely transferred from the dopants to the host materials. The host materials are generally pure organic compounds, and cannot utilize the energy of triplet excitons. As a result, the luminescent efficiency of OLED will be lost. With respect to blue phosphorescent host materials, it is relatively hard to achieve because the blue phosphorescent host materials themselves have relatively high $E_T$, and the host materials cannot satisfy the requirement until they have higher $E_T$. Thus, it is hard from the viewpoint of molecular design.

It can be seen that the relatively lower triplet energy level of the existing host materials is likely to cause the OLED to have relatively low efficiency.

SUMMARY OF INVENTION

To address the aforesaid and other problems, the present invention provides imidazole[4,5-f][1,10]phenanthroline derivatives, methods of preparing the same, and use thereof, for improving the efficiency of OLED devices, thereby improving the display quality.

An embodiment of the present invention provides imidazole[4,5-f][1,10]phenanthroline derivatives conforming to the chemical structural formula of:

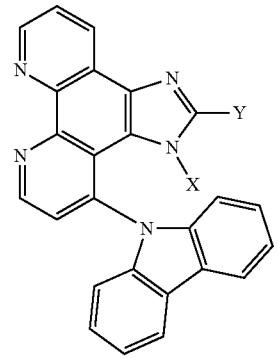

wherein X and Y are independently selected from the group consisting of Z-substituted aryl ring, Z-substituted heteroaryl ring, unsubstituted aryl ring, or unsubstituted heteroaryl ring, and can be identical or different wherein Z is independently selected from the group consisting of aryl, $C_{1-4}$ alkoxy, amino, nitro, trifluoromethyl, cyano, halo atom, or $C_{1-24}$ aliphatic hydrocarbyl.

In an aspect, the unsubstituted aryl ring comprises phenyl, biphenylyl, naphthyl, anthryl, phenanthryl, or pyrenyl.

In another aspect, the unsubstituted heteroaryl ring comprise pyridyl, bipyridylyl, indolyl, quinolyl, or thienyl.

In still another aspect, the C1-24 aliphatic hydrocarbyl comprises $C_{1-24}$ linear alkyl, branched alkyl, cyclic alkyl, linear alkenyl, branched alkenyl, cyclic alkenyl, linear alkynyl, branched alkynyl, or cyclic alkynyl.

In a preferable aspect, the imidazole[4,5-f][1,10]phenanthroline derivatives are selected from the group consisting of:
11-(nonahydrogen-carbazol-9-yl)-1,2-di-phenyl-monohydrogen-imidazole[4,5-f][1,10]phenanthroline wherein X and Y are both phenyl;
11-(nonahydrogen-carbazol-9-yl)-1,2-dimethylphenyl-monohydrogen-imidazole[4,5-f][1,10]phenanthroline wherein X and Y are both methylphenyl;
11-(nonahydrogen-carbazol-9-yl)-2-phenyl-1-(pyridin-4-yl)-monohydrogen-imidazole[4,5-f][1,10]phenanthroline wherein X is pyridyl, Y is phenyl;
11-(nonahydrogen-carbazol-9-yl)-1-phenyl-2-(thien-2-yl)-monohydrogen-imidazole[4,5-f][1,10]phenanthroline wherein X is phenyl, Y is thienyl; or
11-(nonahydrogen-carbazol-9-yl)-2-phenyl-1-(pyren-2-yl)-monohydrogen-imidazole[4,5-f][1,10]phenanthroline wherein X is pyrenyl, Y is phenyl.

Another embodiment of the present invention provides a method of preparing the imidazole[4,5-f][1,10]phenanthroline derivatives in accordance with the present invention, said method comprising:

oxidizing 4-chloro-1,10-phenanthroline to generate 4-chloro-1,10-phenanthroline-5,6-dione;

cyclizing the resultant 4-chloro-1,10-phenanthroline-5,6-dione with an aldehyde Y—CHO and an amine X—$NH_2$ in the presence of ammonium acetate to produce an imidazole[4,5-f][1,10]phenanthroline substituted with Cl, X and Y; and removing hydrogen chloride from the imidazole[4,5-f][1,10]phenanthroline substituted with Cl, X and Y by reaction with carbazole in the presence of sodium hydride to produce the desired imidazole[4,5-f][1,10]phenanthroline derivatives.

Still another embodiment of the present invention provides an organic light-emitting device (OLED) comprising a luminescent layer prepared by a host material and a dopant wherein the host material is any one of the imidazole[4,5-f][1,10]phenanthroline derivatives as described above.

In an aspect, the imidazole[4,5-f][1,10]phenanthroline derivatives comprise 85 wt % to 98 wt % of the luminescent layer.

In another aspect, the luminescent layer has a thickness of 20 nm to 50 nm, for example, the luminescent layer has a thickness of 20 nm, 25 nm, 30 nm, 36 nm, 40 nm, 45 nm, or 50 nm.

Still another embodiment of the presents invention provides a display comprising any one of the organic light-emitting devices as described above.

DETAILED DESCRIPTION OF THE INVENTION

To address the problem that the existing organic light-emitting device has relatively low efficiency, the present invention provides imidazole[4,5-f][1,10]phenanthroline derivatives, methods of preparing the same, and use thereof. In the embodiments, carbazole group and X group are introduced to 11-site and 1-site of imidazole[4,5-f][1,10]phenanthroline, respectively. Because of the sterically hindered effect of carbazole group and X group, warping occurs between the hole-transporting carbazole group and the electron-transporting phenanthroline group, facilitates maintaining the molecules at relatively higher triplet energy level, and thus can be used as the host material of the luminescent layer. Moreover, the imidazole[4,5-f][1,10]phenanthroline in the molecule can transport electrons, and the carbazole can transport holes; thus the molecule possess bipolar transporting properties, and facilitates improving the efficiency of OLED.

For describing the objects, technical solutions, and advantages of the present invention more clearly, hereinafter it is further described in details.

An embodiment of the present invention provides imidazole[4,5-f][1,10]phenanthroline derivatives conforming to the chemical structural formula of:

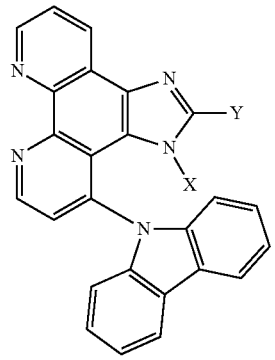

wherein X and Y are independently selected from the group consisting of Z-substituted aryl ring, Z-substituted heteroaryl ring, unsubstituted aryl ring, or unsubstituted heteroaryl ring, and they can be identical or different wherein Z is aryl, C1-4 alkoxy, amino, nitro, trifluoromethyl, cyano, halo atom, or $C_{1-24}$ aliphatic hydrocarbyl. Of those, Z is used to adjust slightly the luminescent color and the electron-transporting property of the molecule, and generally selected from electron-withdrawing group, or electron-donating group. For instance, aryl, $C_{1-4}$ alkoxy, amino and $C_{1-24}$ aliphatic hydrocarbyl are generally used as electron-donating groups, while nitro, trifluoromethyl, cyano and halo atom are generally used as electron-withdrawing groups.

Preferably, the unsubstituted aryl ring comprises phenyl, biphenylyl, naphthyl, anthryl, phenanthryl, or pyrenyl.

Preferably, the unsubstituted heteroaryl ring comprises pyridyl, bipyridylyl, indolyl, quinolyl, or thienyl.

Preferably, the $C_{1-24}$ aliphatic hydrocarbyl comprises $C_{1-24}$ linear alkyl, branched alkyl, cyclic alkyl, linear alkenyl, branched alkenyl, cyclic alkenyl, linear alkynyl, branched alkynyl, or cyclic alkynyl.

Preferably, the imidazole[4,5-f][1,10]phenanthroline derivatives are selected from the group consisting of:

11-(nonahydrogen-carbazol-9-yl)-1,2-di-phenyl-monohydrogen-imidazole[4,5-f][1,10]phenanthroline wherein X and Y are both phenyl;

11-(nonahydrogen-carbazol-9-yl)-1,2-dimethylphenyl-monohydrogen-imidazole[4,5-f][1,10]phenanthroline wherein X and Y are both methylphenyl;

11-(nonahydrogen-carbazol-9-yl)-2-phenyl-1-(pyridin-4-yl)-monohydrogen-imidazole[4,5-f][1,10]phenanthroline wherein X is pyridyl, Y is phenyl;

11-(nonahydrogen-carbazol-9-yl)-1-phenyl-2-(thien-2-yl)-monohydrogen-imidazole[4,5-f][1,10]phenanthroline wherein X is phenyl, Y is thienyl; or 11-(nonahydrogen-carbazol-9-yl)-2-phenyl-1-(pyren-2-yl)-monohydrogen-imidazole[4,5-f][1,10]phenanthroline wherein X is pyrenyl, Y is phenyl.

Another embodiment of the present invention provides a method of preparing the imidazole[4,5-f][1,10]phenanthroline derivatives comprising:

(a) oxidizing 4-chloro-1,10-phenanthroline to produce 4-chloro-1,10-phenanthroline-5,6-dione;

(b) cyclizing the resultant 4-chloro-1,10-phenanthroline-5,6-dione with an aldehyde Y—CHO and an amine X—$NH_2$ in the presence of ammonium acetate to produce an imidazole[4,5-f][1,10]phenanthroline substituted with Cl, X and Y; and (c) removing hydrogen chloride from the imidazole[4,5-f][1,10]phenanthroline substituted with Cl, X and Y by reaction with carbazole in the presence of sodium hydride to produce the desired imidazole[4,5-f][1,10] phenanthroline derivatives.

Of those, in (a), the oxidization may be, e.g., carried out as follows: With stirring, 4-chloro-1,10-phenanthroline (20 mmol) and KBr (30 mmol) are sequentially and slowly added into concentrated sulfuric acid (30 ml) in an ice bath. Then, fuming nitric acid (15 mL, 86 wt % to 97.5 wt %) is added into the above-formed solution. The mixture is stirred in the ice bath for additional 30 minutes, and then heated to reflux for 5 hours. After completion of reaction, the liquid is poured into ice water (320 g), and neutralized with 10 M aqueous NaOH solution. Then, the mixture is extracted with 50 ml dichloromethane (8×). The extracted liquid is dried over anhydrous sodium sulfate, filtered, and evaporated to remove solvent to give raw 4-chloro-1,10-phenanthroline-5,6-dione. The raw product is re-crystallized with methanol to give 4-chloro-1,10-phenanthroline-5,6-dione.

In (b), the cyclization may be, e.g., carried out as follows: 4-chloro-1,10-phenanthroline-5,6-dione (20 mmol), Y—CHO (20 mmol), X—$NH_2$ (30 mmol) and ammonium acetate (20 g) are added into glacial acetic acid (120 mL), and heated to reflux under argon atmosphere for 24 hours. Then, the reaction mixture is cooled to room temperature, poured into methanol, and filtered to give raw imidazole[4,5-f][1,10]phenanthroline. The resultant raw product is further purified with column chromatography to give imidazole[4,5-f][1,10]phenanthroline substituted with Cl, X and Y.

In (c), the HCl removal may be, e.g., carried out as follows: NaH (30 mmol) is added into DMF under nitrogen atmosphere, and then a solution of carbazole (20 mmol) in DMF is dropwise added thereto with protection of ice water bath. After adding, the solution is warmed to room temperature, and a solution of imidazole[4,5-f][1,10]phenanthroline compound (25 mmol) in DMF is added to the solution. The reaction is stirred for 2 hours. The reaction mixture is poured into methanol, and extracted with ethyl acetate and distilled water. The organic solvent is removed from the organic layer, thereby giving a raw imidazole[4,5-f][1,10]phenanthroline derivative. The raw product is purified with column chromatography to give the desired imidazole[4,5-f][1,10] phenanthroline derivative.

Still another embodiment of the present invention provides an organic light-emitting device comprising a luminescent layer prepared by a host material and a dopant wherein the host material is any one of the imidazole[4,5-f][1,10]phenanthroline derivatives as described above. The imidazole[4,5-f][1,10]phenanthroline derivatives in accordance with the present invention have relative high triplet energy level, and thus are particularly suitable for blue phosphorescent host material, and facilitates improving the efficiency of the OLED.

The dopant suitable for use in the embodiments of the present invention can be conventional dopants for use in luminescent layers in the art, such as, bis(4,6-difluorophenylpyridin-N,C2)pyridinecarbonyl iridium (Flrpic), bis(4,6-difluorophenylpyridine)-5-(pyridin-2-yl)-1H-tetrazol iridium(III) (FlrN4), or bis(4,6-difluorophenylpyridine)-3-(trifluoromethyl)-5-(pyridin-2-yl)-1,2,4-triazole iridium(III) (Flrtaz). Preferably, the imidazole[4,5-f][1,10]phenanthroline derivatives comprise 85 wt % to 98 wt % of the luminescent layer, and the dopant comprises 2% to 15% of the luminescent layer. Any weight percent of the host material exceeding the aforesaid range is not favorable for energy transferring of the dopant and the host material or for electron or hole transporting of the luminescent layer, and thus will reduce the efficiency of the device.

Preferably, the luminescent layer has a thickness of 20 nm to 50 nm, for example, the luminescent layer may have a thickness of 20 nm, 25 nm, 30 nm, 36 nm, 40 nm, 45 nm, or 50 nm.

Still another embodiment of the present invention provide a display comprising any one of the organic light-emitting devices as described above. The displays can comprise, but are not limited to, liquid crystal panels, electronic papers, OLED panels, liquid crystal televisions, liquid crystal displays, digital frames, mobile phones, tablet computers, and the like, or a display component thereof.

In the technical solutions of the present invention, the 4-chloro-1,10-phenanthroline is first oxidized to produce 4-chloro-1,10-phenanthroline-5,6-dione, which is then cyclized, together with introduction of X and Y groups, and finally carbazole group is introduced to form the imidazole [4,5-f][1,10]phenanthroline derivatives in accordance with the embodiments of the present invention. Because of the sterically hindered effect of carbazole group and X group, warping occurs between the hole-transporting carbazole group and the electron-transporting phenanthroline group, facilitates maintaining the molecules at relatively higher triplet energy level, and thus can be used as the host material of the luminescent layer. Moreover, the imidazole[4,5-f][1,10]phenanthroline in the molecule can transport electrons, and the carbazole can transport holes; thus the molecule possess bipolar transporting properties, and facilitates improving the efficiency of OLED.

Hereinafter the present invention is further described with reference to the following examples, but the present invention is not limited thereto.

EXAMPLES

Preparation Example

Preparation of
4-Chloro-1,10-Phenanthroline-5,6-Dione

With stirring, 4-chloro-1,10-phenanthroline (20 mmol) and KBr (30 mmol) were sequentially and slowly added into concentrated sulfuric acid (30 mmol) in an ice bath, and then fuming nitric acid (15 mL, 86 wt % to 97.5 wt %) was added into the aforesaid solution. The reaction mixture was stirred in the ice bath for additional 30 minutes, and then heated to reflux for 5 hours. After reaction, the liquid was poured into ice water (320 g), and neutralized with 10 M NaOH until pH=7.0. Next, the mixture was extracted with 50 mL dichloromethane (8×). The extracted liquid was dried over anhydrous sodium sulfate, filtered, and evaporated to remove solvent to give raw 4-chloro-1,10-phenanthroline-5,6-dione. The raw product was re-crystallized with methanol to give 4-chloro-1,10-phenanthroline-5,6-dione (3.8 g) with a yield of 77.5%. The obtained 4-chloro-1,10-phenanthroline-5,6-dione was analyzed and identified with mass spectrum (MS) and Elemental Analysis, respectively.

MS Data: m/z: 244.00 (100.0%), 246.00 (32.1%), 245.01 (13.1%), 247.00 (4.4%), 246.01 (1.2%); Elemental Analysis Data: C, 58.92; H, 2.06; Cl, 14.49; N, 11.45; O, 13.08.

The 4-chloro-1,10-phenanthroline-5,6-dione as prepared above was used for the preparation of the imidazole[4,5-f][1,10]phenanthroline derivatives of Examples 1 to 5.

Example 1

Preparation of 11-(nonahydrogen-carbazol-9-yl)-1,2-di-phenyl-monohydrogen-imidazole[4,5-f][1,10]phenanthroline

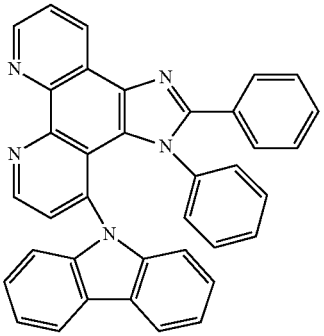 [SMILES: c1ccc(-c2nc3c4cccnc4c4nccc(-n5c6ccccc6c6ccccc65)c4c3n2-c2ccccc2)cc1]

The title compound was prepared as follows:
(1) 4-chloro-1,10-phenanthroline-5,6-dione (20 mmol), benzaldehyde (20 mmol), aniline (30 mmol) and ammonium acetate (20 g) were added into glacial acetic acid (120 mL), and heated to reflux under argon atmosphere for 24 hours. After completion of reaction, the reaction mixture was cooled to room temperature, poured into methanol (150 ml), and filtered to give raw 11-chloro-1,2-di-phenyl-monohydrogen-imidazole[4,5-f][1,10]phenanthroline. The resultant raw product was further purified with column chromatography to give 11-chloro-1,2-di-phenyl-monohydrogen-imidazole[4,5-f][1,10]phenanthroline (5.8 g) with a yield of 71.3%. The obtained 11-chloro-1,2-di-phenyl-monohydrogen-imidazole[4,5-f][1,10]phenanthroline was analyzed and identified with MS and Elemental Analysis, respectively.

MS Data: m/z: 406.10 (100.0%), 408.10 (32.4%), 407.10 (28.7%), 409.10 (8.8%), 408.11 (3.6%), 410.10 (1.3%); Elemental Analysis Data: C, 73.80; H, 3.72; Cl, 8.71; N, 13.77.

(2) Under nitrogen atmosphere, sodium hydride (NaH) (30 mmol) was added into N,N-dimethylformamide (DMF) (100 ml), and then a solution of carbazole (20 mmol) in DMF (100 ml) was added thereto with protection of ice water bath. After adding, the solution was warmed to room temperature, and a solution of 11-chloro-1,2-di-phenyl-monohydrogen-imidazole[4,5-f][1,10]phenanthroline compound (25 mmol) in DMF (100 ml) was dropwise added. The reaction was stirred for 2 hours. The reaction mixture was poured into 150 ml methanol, and extracted with ethyl acetate (100 ml) and distilled water (150 ml). The organic layer was separated, and distilled under reduced pressured to remove the organic solvent in the organic layer, thereby giving the raw product of the target compound. The raw product was purified with column chromatography to give 11-(nonahydrogen-carbazol-9-yl)-1,2-di-phenyl-monohydrogen-imidazole[4,5-f][1,10]phenanthroline (6.0 g) with a yield of 55.8%. The obtained 11-(nonahydrogen-carbazol-9-yl)-1,2-di-phenyl-monohydrogen-imidazole[4,5-f][1,10]phenanthroline was analyzed and identified with MS, Elemental Analysis, and Nuclear Magnetic Resonance (NMR), respectively.

MS Data: m/z: 537.20 (100.0%), 538.20 (40.3%), 539.20 (8.6%), 538.19 (1.8%), 540.21 (1.0%); Elemental Analysis Data: C, 82.66; H, 4.31; N, 13.03; NMR Data: $^1$H NMR (400 MHz, CDCl$_3$, δ): 8.8 (d, 2H), 8.55 (d, 1H), 8.19 (d, 1H), 8.0 (d, 1H), 7.55-7.40 (m, 10H), 7.3-7.08 (m, 8H).

Example 2

Preparation of 11-(nonahydrogen-carbazol-9-yl)-1,2-dimethylphenyl-monohydrogen-imidazole[4,5-f][1,10]phenanthroline

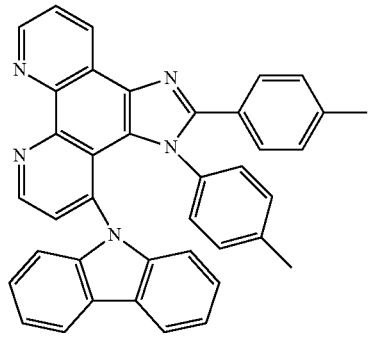 [SMILES: Cc1ccc(-c2nc3c4cccnc4c4nccc(-n5c6ccccc6c6ccccc65)c4c3n2-c2ccc(C)cc2)cc1]

The title compound was prepared as follows:
(1) 4-chloro-1,10-phenanthroline-5,6-dione (20 mmol), p-methylbenzaldehyde (20 mmol), p-methylaniline (30 mmol) and ammonium acetate (20 g) were added into glacial acetic acid (120 ml), and heated to reflux under argon atmosphere for 24 hours. After completion of reaction, the reaction mixture was cooled to room temperature, poured into 150 ml methanol, and filtered to give raw 11-chloro-1,2-dimethylphenyl-monohydrogen-imidazole[4,5-f][1,10]phenanthroline. The resultant raw product was further purified with column chromatography to give 11-chloro-1,2-dimethylphenyl-monohydrogen-imidazole[4,5-f][1,10]phenanthroline (6.1 g) with a yield of 70.1%. The obtained 11-chloro-1,2-dimethylphenyl-monohydrogen-imidazole[4,5-f][1,10]phenanthroline was analyzed and identified with MS and Elemental Analysis, respectively.

MS Data: m/z: 434.13 (100.0%), 436.13 (32.4%), 435.13 (30.7%), 437.13 (9.5%), 436.14 (4.2%), 438.13 (1.5%); Elemental Analysis Data: C, 74.56; H, 4.40; Cl, 8.15; N, 12.88.

(2) Under nitrogen atmosphere, NaH (30 mmol) was added into DMF (100 ml), and a solution of carbazole (20 mmol) in DMF (100 ml) was dropwise added thereto with protection of ice water bath. After adding, the solution was warmed to room temperature, and a solution of 11-chloro-1,2-dimethylphenyl-monohydrogen-imidazole[4,5-f][1,10]phenanthroline compound (25 mmol) in DMF (100 ml) was added. The reaction was stirred for 2 hours. Next, the reaction mixture was poured into 150 ml methanol, and was extracted with 100 ml ethyl acetate and 150 distilled water. The organic layer was separated, distilled under reduced pressure to remove the organic solvent in the organic layer, to give the raw product of the target compound. The raw product was purified with column chromatography to give 11-(nonahydrogen-carbazol-9-yl)-1,2-dimethylphenyl-monohydrogen-imidazole[4,5-f][1,10]phenanthroline (5.6 g) with a yield of 49.6%. The 11-(nonahydrogen-carbazol-9-yl)-1,2-dimethylphenyl-monohydrogen-imidazole[4,5-f][1,10]phenanthroline was analyzed and identified with MS, Elemental Analysis, and NMR.

MS Data: m/z: 565.23 (100.0%), 566.23 (42.5%), 567.23 (9.5%), 566.22 (1.8%), 568.24 (1.2%); Elemental Analysis Data: C, 82.81; H, 4.81; N, 12.38; NMR Data: $^1$H NMR (400 MHz, CDCl$_3$, δ): 8.8 (d, 2H), 8.55-8.52 (m, 3H), 8.19(d, 1H), 8.0 (d, 1H), 7.45-7.4(m, 6H), 7.3-7.08(m,8H), 2.43 (s,3H), 2.34(s,3H).

Example 3

Preparation of 11-(nonahydrogen-carbazol-9-yl)-2-phenyl-1-(pyridin-4-yl)-monohydrogen-imidazole[4,5-f][1,10]phenanthroline

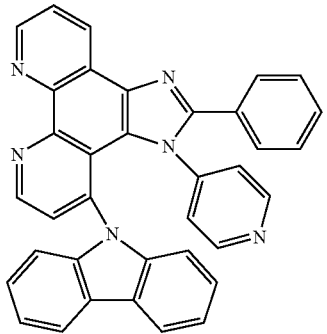 [SMILES: c1ccc(-c2nc3c4cccnc4c4nccc(-n5c6ccccc6c6ccccc65)c4c3n2-c2ccncc2)cc1]

The title compound was prepared as follows:
(1) 4-chloro-1,10-phenanthroline-5,6-dione (20 mmol), benzaldehyde (20 mmol), 4-aminopyridine (30 mmol) and ammonium acetate (20 g) were added into glacial acetic acid (120 ml), and heated to reflux under argon atmosphere for 24 hours. After completion of reaction, the reaction was cooled to room temperature, poured into 150 ml methanol, and filtered to give raw 11-chloro-2-phenyl-1-(pyridin-4-yl)-monohydrogen-imidazole[4,5-f][1,10]phenanthroline. The obtained raw product was further purified with column chromatography to give 11-chloro-2-phenyl-1-(pyridin-4-yl)-monohydrogen-imidazole[4,5-f][1,10]phenanthroline (5.2 g) with a yield of 63.7%. The obtained 11-chloro-1,2-dimethylphenyl-monohydrogen-imidazole[4,5-f][1,10]phenanthroline was analyzed and identified with MS and Elemental Analysis, respectively.

MS Data: m/z: 407.09 (100.0%), 409.09 (32.5%), 408.10 (26.1%), 410.09 (8.9%), 409.10 (3.3%), 408.09 (1.8%), 411.10 (1.1%); Elemental Analysis Data: C, 70.68; H, 3.46; Cl, 8.69; N, 17.17.

(2) Under nitrogen atmosphere, NaH (30 mmol) was added into DMF (100 ml), and a solution of carbazole (20 mmol) in DMF (100 ml) was dropwise added thereto with protection of ice water bath. After adding, the solution was warmed to room temperature, and a solution of 11-chloro-2-phenyl-1-(pyridin-4-yl)-monohydrogen-imidazole[4,5-f][1,10]phenanthrolinein (25 mmol) in DMF (100 ml) was added. Then, the reaction was stirred for 2 hours. The reaction mixture was poured into 150 ml methanol, and was extracted with 100 ml ethyl acetate and 150 distilled water. The organic layer was separated, evaporated under reduced pressure to remove the organic solvent in the organic layer, to give the raw product of the target compound. The raw product was purified with column chromatography to give 11-(nonahydrogen-carbazol-9-yl)-2-phenyl-1-(pyridin-4-yl)-monohydrogen-imidazole[4,5-f][1,10]phenanthroline (6.7 g) with a yield of 62.0%. The obtained 11-(nonahydrogen-carbazol-9-yl)-2-phenyl-1-(pyridin-4-yl)-monohydrogen-imidazole[4,5-f][1,10]phenanthroline was analyzed and identified with MS, Elemental Analysis and NMR, respectively.

MS Data: m/z: 538.19 (100.0%), 539.19 (41.2%), 540.20 (7.5%); Elemental Analysis Data: C, 80.28; H, 4.12; N, 15.60; NMR Data: $^1$H NMR (400 MHz, CDCl$_3$, δ): 8.8 (d, 2H), 8.6-8.55 (m, 3H), 8.19(d, 1H), 8.0 (d, 1H), 7.5-7.4(m, 9H), 7.3-7.08 (m,6H).

Example 4

Preparation of 11-(nonahydrogen-carbazol-9-yl)-1-phenyl-2-(thien-2-yl)-monohydrogen-imidazole[4,5-f][1,10]phenanthroline

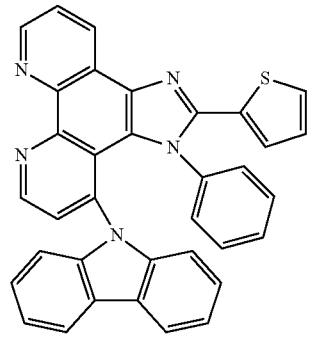 [SMILES: c1ccc(-n2c(-c3cccs3)nc3c4cccnc4c4nccc(-n5c6ccccc6c6ccccc65)c4c32)cc1]

The title compound was prepared as follows:
(1) 4-chloro-1,10-phenanthroline-5,6-dione (20 mmol), benzaldehyde (20 mmol), 2-aminothiophene (30 mmol) and ammonium acetate (20 g) were added into glacial acetic acid (120 ml), and heated to reflux under argon atmosphere for 24 hours. After completion of reaction, the reaction was cooled to room temperature, the reaction mixture was poured into 150 ml methanol, and filtered to give raw 11-chloro-1-phenyl-2-(thien-2-yl)-monohydrogen-imidazole[4,5-f][1,10]phenanthroline. The obtained raw product was further purified with column chromatography to give 11-chloro-1-phenyl-2-(thien-2-yl)-monohydrogen-imidazole[4,5-f][1,10]phenanthroline (5.7 g) with a yield of 69.0%. the obtained 11-chloro-1-phenyl-2-(thien-2-yl)-monohydrogen-imidazole[4,5-f][1,10]phenanthroline was analyzed and identified with MS and Elemental Analysis, respectively.

MS Data: m/z: 412.05 (100.0%), 414.05 (36.5%), 413.06 (25.0%), 415.06 (8.1%), 414.06 (3.6%), 413.05 (2.3%), 415.05 (1.9%), 416.05 (1.7%), 416.06 (1.1%); Elemental Analysis Data: C, 66.90; H, 3.17; Cl, 8.59; N, 13.57; S, 7.77

(2) Under nitrogen atmosphere, NaH (30 mmol) was added into DMF (100 ml), and a solution of carbazole (20 mmol) in DMF (100 ml) was dropwise added thereto with protection of ice water bath. After adding, the solution was warmed to room temperature, and a solution of 11-chloro-1-phenyl-2-(thien-2-yl)-monohydrogen-imidazole[4,5-f][1,10]phenanthrolinein (25 mmol) in DMF (100 ml) was dropwise added. Then, the reaction was stirred for 2 hours. The reaction mixture was poured into 150 ml methanol, and was extracted with 100 ml ethyl acetate and 150 distilled water. The organic layer was separated, evaporated under reduced pressure to remove the organic solvent in the organic layer, to give the raw product of the target compound.

The raw product was purified with column chromatography to give 11-(nonahydrogen-carbazol-9-yl)-1-phenyl-2-(thien-2-yl)-monohydrogen-imidazole[4,5-f][1,10]phenanthroline (7.0 g) with a yield of 64.4%. The obtained 11-(nonahydrogen-carbazol-9-yl)-1-phenyl-2-(thien-2-yl)-monohydrogen-imidazole[4,5-f][1,10]phenanthroline was analyzed and identified with MS, Elemental Analysis and NMR, respectively.

MS Data: m/z: 543.15 (100.0%), 544.16 (38.1%), 545.16 (7.1%), 545.15 (5.5%), 544.15 (2.6%), 546.15 (1.7%), 546.16 (1.0%); Elemental Analysis Data: C, 77.33; H, 3.89; N, 12.88; S, 5.90; NMR Data: $^1$H NMR (400 MHz, CDCl$_3$, δ): 8.8 (d, 2H), 8.55 (d, 1H), 8.19(d, 1H), 8.0 (d, 1H), 7.78 (d,1H),7.55(m,3H), 7.40(d, 2H), 7.3-7.08(m,9H), 7.0(d,1H).

Example 5

Preparation of 11-(nonahydrogen-carbazol-9-yl)-2-phenyl-1-(pyren-2-yl)-monohydrogen-imidazole[4,5-f][1,10]phenanthroline

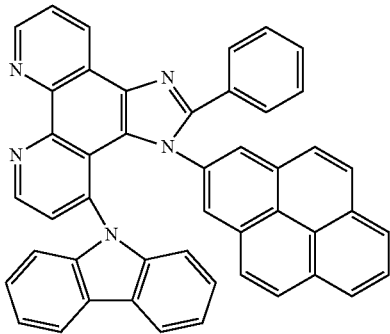 [SMILES: c1ccc(-c2nc3c4cccnc4c4nccc(-n5c6ccccc6c6ccccc65)c4c3n2-c2cc3ccc4cccc5ccc(c2)c3c45)cc1]

The title compound was prepared as follows:
(1) 4-chloro-1,10-phenanthroline-5,6-dione (20 mmol), pyrenylaldehyde (20 mmol), aniline (30 mmol) and ammonium acetate (20 g) were added into glacial acetic acid (120 ml), and heated to reflux under argon atmosphere for 24 hours. After completion of reaction, the reaction was cooled to room temperature, and poured into 150 ml methanol. and filtered to give raw 11-chloro-2-phenyl-1-(pyren-2-yl)-monohydrogen-imidazole[4,5-f][1,10]phenanthroline. The obtained raw product was further purified with column chromatography to give 11-chloro-2-phenyl-1-(pyren-2-yl)-monohydrogen-imidazole[4,5-f][1,10]phenanthroline (5.5 g) with a yield of 51.8%. The obtained 11-chloro-2-phenyl-1-(pyren-2-yl)-monohydrogen-imidazole[4,5-f][1,10]phenanthroline was analyzed and identified with MS and Elemental Analysis, respectively.

MS Data: m/z: 530.13 (100.0%), 531.13 (39.3%), 532.13 (32.5%), 533.13 (12.3%), 532.14 (7.0%), 534.13 (2.4%); Elemental Analysis Data: C, 79.17; H, 3.61; Cl, 6.68; N, 10.55.

(2) Under nitrogen atmosphere, NaH (30 mmol) was added into DMF (100 ml), and a solution of carbazole (20 mmol) in DMF (100 ml) was dropwise added thereto with protection of ice water bath, After adding, the solution was warmed to room temperature, and a solution of 11-chloro-2-phenyl-1-(pyren-2-yl)-monohydrogen-imidazole[4,5-f][1,10]phenanthrolinein (25 mmol) in DMF (100 ml) was added. Then, the reaction was stirred for 2 hours. The reaction mixture was poured into 150 ml methanol, and was extracted with 100 ml ethyl acetate and 150 distilled water. The organic layer was separated, evaporated under reduced pressure to remove the organic solvent in the organic layer, to give the raw product of the target compound.

The raw product was purified with column chromatography to give 11-(nonahydrogen-carbazol-9-yl)-2-phenyl-1-(pyren-2-yl)-monohydrogen-imidazole[4,5-f][1,10]phenanthroline 7.4 g with a yield of 55.9%. The obtained 11-(nonahydrogen-carbazol-9-yl)-2-phenyl-1-(pyren-2-yl)-monohydrogen-imidazole[4,5-f][1,10]phenanthroline was analyzed and identified with MS, Elemental Analysis and NMR, respectively.

MS Data: m/z: 661.23 (100.0%), 662.23 (51.1%), 663.23 (13.6%), 664.24 (2.1%), 662.22 (1.8%); Elemental Analysis Data: C, 85.30; H, 4.11; N, 10.58; NMR Data: $^1$H NMR (400 MHz, CDCl$_3$, δ): 8.8 (d, 2H), 8.55 (d, 1H), 8.19(d, 1H), 8.0 (d, 5H), 7.8(t,1H), 7.7(d,4H),7.50-7.40 (m, 7H), 7.3-7.08(m, 6H).

Examples 6 to 10 demonstrate the use of imidazole[4,5-f][1,10]phenanthroline derivatives in organic light-emitting devices, wherein the imidazole[4,5-f][1,10]phenanthroline derivatives obtained in accordance with Examples 1 to 5 are used as the host materials of the organic light-emitting devices, respectively, wherein the luminescent layers of the organic light-emitting devices are blue phosphorescent layer.

Example 6

Preparation of Organic Light-Emitting Devices

Indium tin oxide (ITO) was used as anode; N,N'-diphenyl-N,N'-(1-naphthyl)-1,1'-biphenyl-4,4'-diamine (NPB) was used as hole transport material; 3-(biphenyl-4-yl)-5-(4-t-butylphenyl)-4-phenyl-4H-1,2,4-triazole (TAZ) was used as electron transfer material; bis(4,6-difluorophenylpyridin-N,C2)pyridinecarbonyl iridium(Flrpic) was used as blue dopant; the 11-(nonahydrogen-carbazol-9-yl)-1,2-di-phenyl-monohydrogen-imidazole[4,5-f][1,10]phenanthroline prepared in accordance with Example 1 of the present invention was used as the host material of the luminescent layer; and lithium fluoride (LiF) was used as electron-injecting material; and aluminum (Al) was used as cathode. The organic light-emitting devices were produced in accordance with conventional processes. The produced organic light-emitting device had a structure of: ITO/NPB (30 nm)/11-(nonahydrogen-carbazol-9-yl)-1,2-di-phenyl-monohydrogen-imidazole[4,5-f][1,10]phen anthroline:Flrpic (8 wt %, 20 nm)/TAZ (30 nm)/LiF (1 nm)/Al (100 nm), wherein 8 wt % meants that the dopant Flrpic comprised 8 wt % of the luminescent layer.

Example 7

Preparation of Organic Light-Emitting Device

ITO was used as anode; NPB was used as hole transport material; TAZ was used as electron transfer material; Flrpic was used as blue dopant; the 11-(nonahydrogen-carbazol-9-yl)-1,2-dimethylphenyl-monohydrogen-imidazole[4,5-f][1,10]phenanthroline prepared in accordance with Example 2 of the present invention was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/11-(nonahydrogen-carbazol-9-yl)-1,2-dimethylphenyl-monohydrogen-imidazole[4,5-f][1,10]phenanthroline:Flrpic (2 wt %, 50 nm)/TAZ (30 nm)/

LiF (1 nm)/Al (100 nm) wherein 2 wt % meant that the dopant Flrpic comprised 2 wt % of the luminescent layer.

Example 8

Preparation of Organic Light-Emitting Device

ITO was used as anode; NPB was used as hole transport material; TAZ was used as electron transfer material; indium (III) bis(4,6-difluorophenylpyridine)-3-(trifluoromethyl)-5-(pyridin-2-yl)-1,2,4-triazole (Flrtaz) was used as blue dopant; the 11-(nonahydrogen-carbazol-9-yl)-2-phenyl-1-(pyridin-4-yl)-monohydrogen-imidazole[4,5-f][1,10]phenanthroline prepared in accordance with Example 3 of the present invention was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/11-(nonahydrogen-carbazol-9-yl)-2-phenyl-1-(pyridin-4-yl)-monohydrogen-imidazole[4,5-f][1,10]phenanthroline:Flrtaz (8 wt %, 30 nm)/TAZ (30 nm)/LiF (1 nm)/Al (100 nm) wherein 8 wt % meant that the dopant Flrtaz comprised 8 wt % of the luminescent layer.

Example 9

Preparation of Organic Light-Emitting Device

ITO was used as anode; NPB was used as hole transport material; TAZ was used as electron transfer material; indium (III) bis(4,6-difluorophenylpyridine)-5-(pyridin-2-yl)-1H-tetrazol (FlrN4) was used as blue dopant; the 11-(nonahydrogen-carbazol-9-yl)-1-phenyl-2-(thien-2-yl)-monohydrogen-imidazole[4,5-f][1,10]phenanthroline prepared in accordance with Example 4 of the present invention was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/11-(nonahydrogen-carbazol-9-yl)-1-phenyl-2-(thien-2-yl)-monohydrogen-imidazole[4,5-f][1,10]phenanthroline:FlrN4(8 wt %, 30 nm)/TAZ (30 nm)/LiF (1 nm)/Al (100 nm) wherein 8 wt % meant that the dopant FlrN4 comprised 8 wt % of the luminescent layer.

Example 10

Preparation of Organic Light-Emitting Device

ITO was used as anode; NPB was used as hole transport material; TAZ was used as electron transfer material; Flrpic was used as blue dopant; the 11-(nonahydrogen-carbazol-9-yl)-2-phenyl-1-(pyren-2-yl)-monohydrogen-imidazole[4,5-f][1,10]phenanthroline prepared in accordance with Example 5 of the present invention was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/11-(nonahydrogen-carbazol-9-yl)-2-phenyl-1-(pyren-2-yl)-monohydrogen-imidazole[4,5-f][1,10]phenanthroline:Flrpic (15 wt %, 20 nm)/TAZ (30 nm)/LiF (1 nm)/Al (100 nm) wherein 15 wt % meant that the dopant Flrpic comprised 15 wt % of the luminescent layer.

Comparative Example 1

ITO was used as anode; NPB was used as hole transport material; TAZ was used as electron transfer material; Flrpic was used as blue dopant; 9,9'-(1,3-phenyl)-di-9H-carbazole (mCP) was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/mCP:Flrpic (2 wt %, 50 nm)/TAZ (30 nm)/LiF (1 nm)/Al (100 nm) wherein 2 wt % meant that the dopant Flrpic comprised 2 wt % of the luminescent layer.

Comparative Example 2

ITO was used as anode; NPB was used as hole transport material; TAZ was used as electron transfer material; indium (III) bis(4,6-difluorophenylpyridine)-3-(trifluoromethyl)-5-(pyridin-2-yl)-1,2,4-triazole (Flrtaz) was used as blue dopant; 9,9'-(1,3-phenyl)-bi-9H-carbazole (mCP) was used as the host material of the luminescent layer; LiF was used as electron-injecting material; and Al was used as cathode. The organic light-emitting devices were produced in accordance with conventional processes. The produced organic light-emitting device had a structure of: ITO/NPB (30 nm)/mCP:Flrtaz (8 wt %, 30 nm)/TAZ (30 nm)/LiF (1 nm)/Al (100 nm) wherein 8 wt % meant that the dopant Flrtaz comprised 8 wt % of the luminescent layer.

Comparative Example 3

ITO was used as anode; NPB was used as hole transport material; TAZ was used as electron transfer material; iridium (III) bis(4,6-difluorophenylpyridine)-5-(pyridin-2-yl)-1H-tetrazol (FlrN4) was used as blue dopant; 9,9'-(1,3-phenyl)-bi-9H-carbazole (mCP) was used as luminescent layer host material; LiF was used as electron-injecting material; and Al was used as cathode. The organic light-emitting devices were produced in accordance with conventional processes. The produced organic light-emitting device had a structure of: ITO/NPB (30 nm)/mCP:FlrN4(8 wt %, 30 nm)/TAZ (30 nm)/LiF (1 nm)/Al (100 nm) wherein 8 wt % meant that the dopant FlrN4 comprised 8 wt % of the luminescent layer.

Test of Organic Light-Emitting Devices

The organic light-emitting devices prepared in accordance with Examples 6 to 10 and Comparative Examples 1 to 3 were measured for electroluminescence spectrum (EL spectrum), luminance (L) and chromaticity (CIE) by using PR650 Type spectrophotometer; and for Current(I)-Voltage (V) characteristic by using Keithley 2400 Source Meter. The results of the aforesaid tests were used to calculate, by using softwares installed in the instruments, External Quantum Efficiency ($\eta_{ext}$, dimensionless) and Luminous Power Efficiency ($\eta_p$, lm/W) of each organic light-emitting device, wherein $\eta_p$ was calculated in accordance with Equation(1), $\eta_{ext}$ was calculated in accordance with Equation (2), and the results were listed in Table 1 below.

$$\eta_p = \frac{L \times \pi}{J \times V}, \quad (1)$$

wherein $\pi=3.1416$, L was luminance, J was current density (J=I/A, I was current, A was luminescent area), and V was voltage;

$$\eta_{ext} = \frac{\pi \cdot \sum (\lambda \cdot s(\lambda)) \cdot \Delta\lambda / hc}{J/e}, \quad (2)$$

wherein $\pi=3.1416$, $\lambda$ was wavelength of EL spectrum, $s(\lambda)$ was electroluminescent intensity of EL spectrum (EL intensity), $\Delta\lambda$ was step length of EL spectrum, h was Planck's constant ($6.63\times10^{-34}$ J·s), c was velocity of light ($3\times10^8$ m/s), J was current density; and e was quantity of elementary charges ($1.6\times10^{-19}$ C).

TABLE 1

| Test Results | Test Results of Organic Light-Emitting Devices | | | | | | | |
|---|---|---|---|---|---|---|---|---|
| | EX. 6 | EX. 7 | EX. 8 | EX. 9 | EX. 10 | Comp. Ex. 1 | Comp. Ex. 2 | Comp. Ex. 3 |
| External Quantum Efficiency $\eta_{ext}$ (%) | 14.6 | 13.5 | 9.2 | 9.0 | 12 | 7.5 | 5.8 | 6.1 |
| Luminous Power Efficiency $\eta_p$ (lm/W) | 26.7 | 24.8 | 6.8 | 7.2 | 20 | 8.9 | 4.4 | 3.2 |

It can be seen from the test results of the organic light-emitting devices prepared in accordance with Examples 6 to 10 and Comparative Examples 1 to 3 that the present invention utilizes imidazole[4,5-f][1,10]phenanthroline derivatives as the host material of the luminescent layer to provide organic light-emitting devices having an External Quantum Efficiency of 9% or greater and a Luminous Power Efficiency of 7 lm/W or greater, especially, Examples 6 and 7 provide organic light-emitting devices having an External Quantum Efficiency of 13% or greater and a Luminous Powder Efficiency of 24 lm/W, which are much greater than those of the organic light-emitting devices prepared in accordance with Comparative Examples 1 to 3 by using existing luminescent layer host materials. The present invention provides a reasonable molecular design of imidazole[4,5-f][1,10]phenanthroline derivatives as bipolar compound, in which the hole transport group carbazole group and the electron transfer group imidazole[4,5-f][1,10]phenanthroline is well connected, and a relatively larger sterically hindered effect formed by X group and carbazole group cause warping to occur in the molecule, so that the molecule has a relatively higher triplet energy level, thereby improving substantially the efficiency of the organic light-emitting devices and maintaining a relatively low efficiency extinction.

It is apparent that persons skilled in the art can make various modifications and variations of the present invention without departing the spirit and scope of the present. As such, provided that these modifications and variations of the present invention fall within the scope of the claims of the present invention and their equivalences, they are intended to be encompassed by the present invention.

The application claims the priority benefit of Chinese Patent Application No. 201310460740.9 filed on Sep. 30, 2013, which is entirely incorporated herein by reference as a portion of the present application.

I claim:

1. An 11-(9H-carbazol-9-yl)-1H-imidazole[4,5-f][1,10] phenanthroline derivative conforming to a chemical structural formula of:

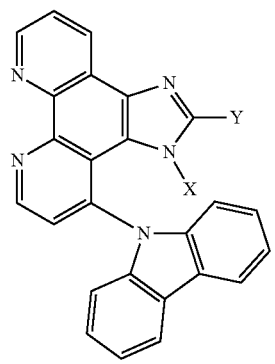

wherein X is independently selected from the group consisting of a Z-substituted heteroaryl ring and an unsubstituted heteroaryl ring, wherein Y is independently selected from the group consisting of a Z-substituted aryl ring, a Z-substituted heteroaryl ring, an unsubstituted aryl ring, and an unsubstituted heteroaryl ring, and wherein Z is independently selected from the group consisting of aryl, $C_{1-4}$ alkoxy, amino, nitro, trifluoromethyl, cyano, halo atom, and $C_{1-24}$ aliphatic hydrocarbyl.

2. The 11-(9H-carbazol-9-yl)-1H-imidazole[4,5-f][1,10] phenanthroline derivative of claim 1, wherein the unsubstituted aryl ring comprises phenyl, biphenylyl, naphthyl, anthryl, phenanthryl, or pyrenyl.

3. The 11-(9H-carbazol-9-yl)-1H-imidazole[4,5-f][1,10] phenanthroline derivative of claim 1, wherein the unsubstituted heteroaryl ring comprises pyridyl, bipyridylyl, indolyl, quinolyl, or thienyl.

4. The 11-(9H-carbazol-9-yl)-1H-imidazole[4,5-f][1,10] phenanthroline derivative of claim 1, wherein the $C_{1-24}$ aliphatic hydrocarbyl comprises $C_{1-24}$ linear alkyl, branched alkyl, cyclic alkyl, linear alkenyl, branched alkenyl, cyclic alkenyl, linear alkynyl, branched alkynyl, or cyclic alkynyl.

5. The 11-(9H-carbazol-9-yl)-1H-imidazole[4,5-f][1,10] phenanthroline derivative of claim 1 is
11-(9H-carbazol-9-yl)-2-phenyl-1-(pyridin-4-yl)-mono-hydrogen-imidazole[4,5-f][1,10]phenanthroline.

6. A method of preparing the imidazole[4,5-f][1,10] phenanthroline derivative of claim 1 comprising:
oxidizing 4-chloro-1,10-phenanthroline to produce 4-chloro-1,10-phenanthroline-5,6-dione;
cyclizing the resultant 4-chloro-1,10-phenanthroline-5,6-dione with an aldehyde Y—CHO and an amine X—NH2 in the presence of ammonium acetate to produce imidazole[4,5-f][1,10]phenanthroline substituted with Cl, X and Y; and
removing hydrogen chloride from the imidazole[4,5-f][1,10]phenanthroline substituted with Cl, X and Y by reaction with carbazole in the presence of sodium hydride.

7. An organic light-emitting device comprising a luminescent layer prepared by a host material and a dopant wherein the host material is an 11-(9H-carbazol-9-yl)-1H-imidazole[4,5-f][1,10]phenanthroline derivative conforming to a chemical structural formula of:

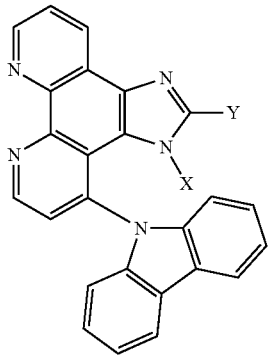

wherein X is independently selected from the group consisting of a Z-substituted heteroaryl ring and an unsubstituted heteroaryl ring, wherein Y is independently selected from the group consisting of a Z-substituted aryl ring, a Z-substituted heteroaryl ring, an unsubstituted aryl ring, and an unsubstituted heteroaryl ring, and wherein Z is independently selected from the group consisting of aryl, $C_{1-4}$ alkoxy, amino, nitro, trifluoromethyl, cyano, halo atom, and $C_{1-24}$ aliphatic hydrocarbyl.

8. The organic light-emitting device of claim 7 wherein the 11-(9H-carbazol-9-yl)-1H-imidazole[4,5-f][1,10]phenanthroline derivatives comprises 85 wt % to 98 wt % of the luminescent layer.

9. The organic light-emitting device of claim 7 wherein the luminescent layer has a thickness of 20 nm to 50 nm.

10. A display comprising the organic light-emitting device of claim 7.

11. The organic light-emitting device of claim 7, wherein the unsubstituted aryl ring comprises phenyl, biphenylyl, naphthyl, anthryl, phenanthryl, or pyrenyl.

12. The organic light-emitting device of claim 7 wherein the unsubstituted heteroaryl ring comprises pyridyl, bipyridylyl, indolyl, quinolyl, or thienyl.

13. The organic light-emitting device of claim 7 wherein the $C_{1-24}$ aliphatic hydrocarbyl comprises $C_{1-24}$ linear alkyl, branched alkyl, cyclic alkyl, linear alkenyl, branched alkenyl, cyclic alkenyl, linear alkynyl, branched alkynyl, or cyclic alkynyl.

14. The organic light-emitting device of claim 7 wherein the 11-(9H-carbazol-9-yl)-1H-imidazole[4,5-f][1,10]phenanthroline derivative is 11-(9H-carbazol-9-yl)-2-phenyl-1-(pyridin-4-yl)-monohydrogen-imidazole[4,5-f][1,10]phenanthroline.

15. The display of claim 10 wherein the 11-(9H-carbazol-9-yl)-1H-imidazole[4,5-f][1,10]phenanthroline derivatives comprises 85 wt % to 98 wt % of the luminescent layer.

16. The display of claim 10 wherein the luminescent layer has a thickness of 20 nm to 50 nm.

* * * * *